(12) United States Patent
Chatterjee et al.

(10) Patent No.: US 6,444,662 B1
(45) Date of Patent: Sep. 3, 2002

(54) STABLE HYPERFORIN SALTS, METHOD FOR PRODUCING SAME AND THEIR USE IN THE TREATMENT OF ALZHEIMER'S DISEASE

(75) Inventors: Shyam Sunder Chatterjee; Clemens Erdelmeier, both of Karlsruhe; Klaus Klessing, Ettlingen; Dieter Marme; Christoph Schächtele, both of Freiburg, all of (DE)

(73) Assignee: Willmar Schwabe GmbH & Co., Karlsruhe (DE)

(*) Notice: Subject to any disclaimer, the term of this patent is extended or adjusted under 35 U.S.C. 154(b) by 0 days.

(21) Appl. No.: 09/622,151

(22) PCT Filed: Feb. 4, 1999

(86) PCT No.: PCT/EP99/00737

§ 371 (c)(1),
(2), (4) Date: Aug. 11, 2000

(87) PCT Pub. No.: WO99/41220

PCT Pub. Date: Aug. 19, 1999

(30) Foreign Application Priority Data

Feb. 13, 1998 (DE) .......................................... 198 05 947

(51) Int. Cl.[7] .......................... C07C 50/36; A61K 35/78
(52) U.S. Cl. .......................... 514/210.01; 514/212.01; 514/218; 514/227.5; 514/231.2; 514/252.1; 514/252.11; 514/256; 514/277; 514/315; 514/365; 514/374; 514/406; 514/408; 514/691; 540/544; 540/575; 540/579; 540/612; 544/59; 544/107; 544/242; 544/358; 544/410; 548/146; 548/235; 548/335.1; 548/373.1; 548/565; 548/579; 548/950; 548/366; 548/374; 536/366; 536/374

(58) Field of Search .................. 514/210.01, 211.01, 514/212.01, 218, 227.5, 231.2, 252.1, 252.11, 256, 277, 315, 365, 374, 396, 406, 408, 691; 540/544, 575, 412; 544/59, 107, 242, 358; 548/410, 146, 235, 335.1, 373.1, 565, 579, 950; 568/366, 374, 389, 457, 459, 503, 507

(56) References Cited

U.S. PATENT DOCUMENTS

| 6,113,907 A | * | 9/2000 | Khwaja et al. | 424/195.1 |
| 6,224,906 B1 | * | 5/2001 | Ghosal | 424/464 |
| 6,238,671 B1 | * | 5/2001 | Joseph | 424/195.1 |

FOREIGN PATENT DOCUMENTS

| DE | 0599307 A | 11/1993 |
| DE | 9713489 | 4/1997 |
| WO | WO-97/13489 A2 * | 4/1997 |

OTHER PUBLICATIONS

Buxbaum, Joseph D., et al., Processing of Alzheimer βA4/amyloid precursor protein: Modulation by agents that regulate protein phosphorylation; Proc. Natl. Acad. Sci, USA, vol. 87, pp. 6003–6006 (Aug., 1990).

Chatterjee, Shyam Sunder, et al., Hyperforin and Hypericun Extract: Interactions with some neurotransmitter systems (abstract); 2nd International Congress on Phytomedicine, (1996).

Games, Dora, et al., Alzheimer–type neuropathology in transgenic mice overexpressing V717Fβ–amyloid precursor protein; Nature, vol. 373, pp. 523–527 (Feb., 1995).

Giacobini, Ezio, Cholinomimetic Therapy of Alzeimer Disease: Does It Slow Down Deterioration?; Int Acad Biomed Drug Res. Basel, Karger, vol. 7, pp. 51–57 (1994).

Hsiao, Karen, et al., Correlative memory Deficits, Aβ Elevation and Amyloid Plaques in Transgenic Mice; Science, vol. 274, pp. 99–102 (Oct., 1996).

Lamb, Bruce T., Presenilins, amyloid–β and Alzheimer's disease, Nature Medicine, vol. 3, n.1; pp. 28–29 (Jan., 1997).

Mendla, Klaus, et al., Die Alzheimer–Krankheit: neue Ansatz in der Pharmakotherapie, PZ Titel, Nr 5 141, pp. 11–16 (Feb., 1996).

EXPRESSION PLASMID (EXAMPLE 34)

Nitsch, Roger M., Release of Alzheimer Amyloid Precursor Derviatives Stimulated by Activation of Muscarnic Acetylcholine Receptors; Science, vol. 258, pp. 304–307 (Oct., 1992).

Scheuner, D., et al., Secreted amyloid β–protein similar to that in the senile plaques of Alzheimer's disease is increased in vivo by the presenilin 1 and 2 and APP mutations linked to familial Alzheimer's disease; Nature Medicine, vol. 2, n.8, pp. 864–870 (Aug., 1996).

\* cited by examiner

*Primary Examiner*—Mukund J. Shah
*Assistant Examiner*—Thomas McKenzie
(74) *Attorney, Agent, or Firm*—Frost Brown Todd LLC

(57) ABSTRACT

Described are salts of hyperforin and adhyperforin of formula I

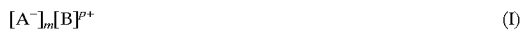

wherein m is an integer from 1 to 3, p is equal to m and gives the total number of positive charges of the residue [B],

Figure 1:
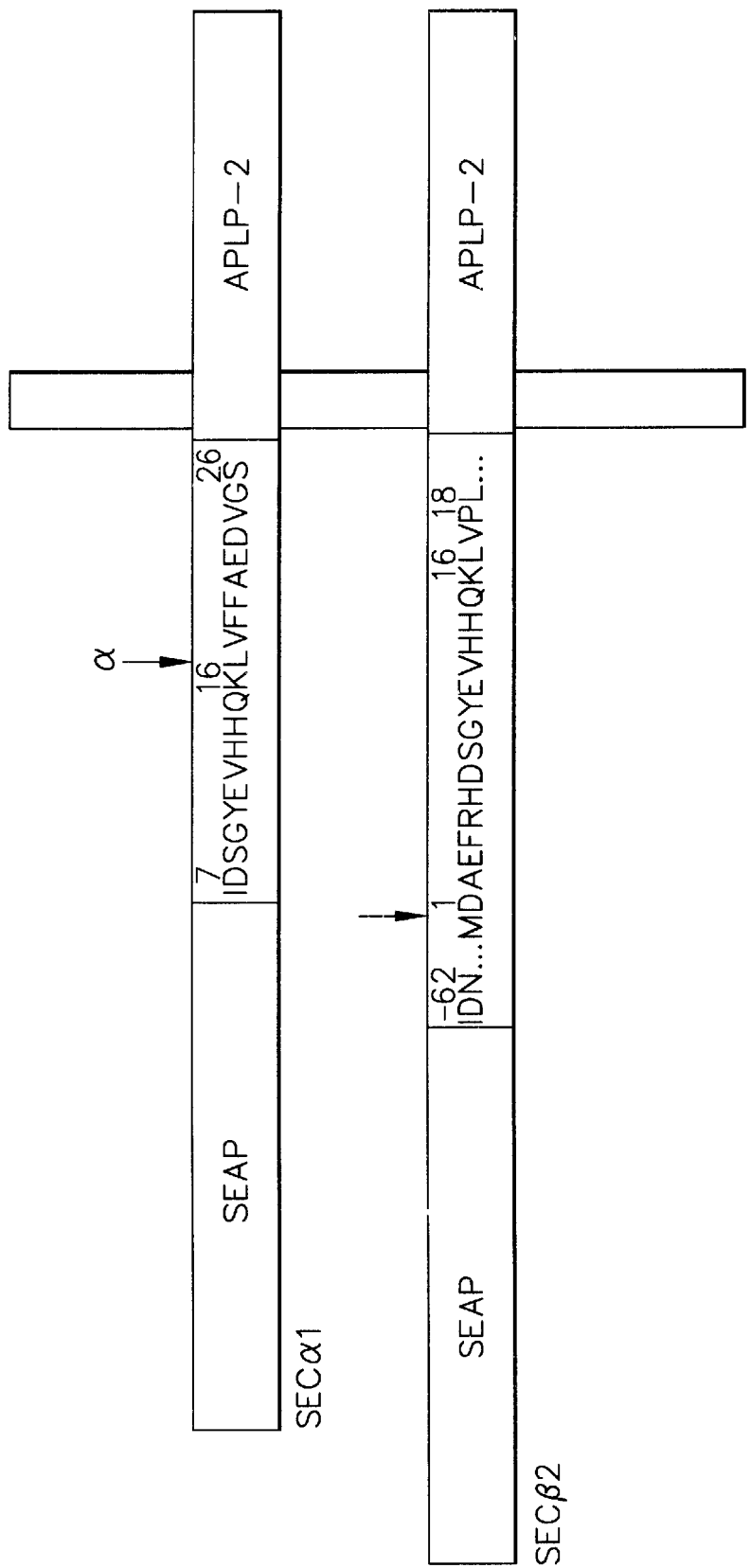

[A$^-$] is an anion of formula II with n=0 or 1

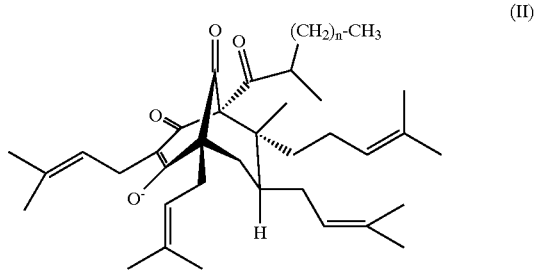

and [B]$^{p+}$ is an ion of an alkali metal or an ammonium ion of a salt-forming nitrogen base of formula III

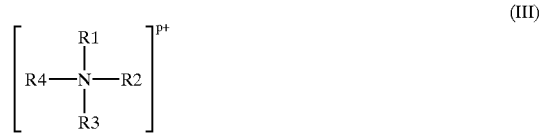

wherein R1 through R4 have a variety of meanings including hydrogen, alkyl, cycloalkyl and similar groups which in turn may be substituted with one or more substituents. The salts serve inter alia for enriching or purifying hyperforin and adhyperforin from St. John's Wort extracts. Pharmaceutical preparations containing the salts are used for treating Alzheimer's Disease.

10 Claims, 1 Drawing Sheet

EXPRESSION PLASMID (EXAMPLE 34)

STABLE HYPERFORIN SALTS, METHOD FOR PRODUCING SAME AND THEIR USE IN THE TREATMENT OF ALZHEIMER'S DISEASE

SUBJECT OF THE INVENTION

The subject of the invention is the provision of stable salts of hyperforin and adhyperforin which are capable of pharmacological activity as they are or by release of the hyperforin or adhyperforin. A fundamental aspect of the invention relates to the provision of a method of enriching or purifying hyperforin and adhyperforin from extracts of St. John's wort by means of precipitation in the form of these stable salts. Another especially important subject of the invention comprises the provision of new active substances for controlling Alzheimer's disease (hereinafter abbreviated to "AD") by treating the cause of the disease.

A further important aspect of the present invention relates to the provision of active-substance combinations which can be used to treat the cause of AD, and at the same time eliminate, considerably improve, or at least halt the progression of psychopathological concomitant phenomena which frequently arise in association with AD, such as anxiety, depressive illnesses, and cognitive disturbances.

BACKGROUND OF THE INVENTION

The amyloid peptide Aβ1–42, a processed product of Alzheimer Precursor Protein APP, plays a central role in the occurrence of AD [Lamb, B. T.: Presenilins, amyloid-β and Alzheimer's Disease. Nature Med. 3 (1997) 28–29. Selkoe, D. J.: Alzheimer's Disease: Genotypes, Pheno-type, and Treatments. Science 275 (1997) 630–631]. This hypothesis is supported by the following experimental findings:

APP Missense mutations (patients with familial AD) lead to an increased release of Aβ1–42 [Scheuner, D. et al.: Secreted amyloid β-protein similar to that in the senile plaques of Alzheimer's disease is increased in vivo by the presenilin 1 and 2 and APP mutations linked to familial Alzheimer's disease. Nature Med. 2 (1996) 864–870].

Mutations in presenilin 1 and presenilin 2 (patients with familial AD) similarly lead to an increase in released Aβ1–42 [Scheuner, D. et al]. Transgenic mice, which overexpress mutated APP, develop age-dependent deposits of Aβ and show cognitive disturbances [Games, D. et al.: Alzheimer-type neuropathology in transgenic mice overexpressing V717F β-amyloid precursor protein. Nature 373 (1995) 523–527. Hsiao, K. et al.: Correlative memory deficits, Aβ Elevation, and Amyloid Plaques in Transgenic Mice. Science 274 (1996) 99–102].

The proteolytic cleavage of the pathogenic Aβ from the Alzheimer Precursor Protein APP is mediated by β- and γ-secretase, the molecular identity of which is unknown. α-Secretase processes APP to a soluble form (sAPP) and a cytoplasmatic residue. The cleavage of α-secretase lies within Aβ, with the result that in this case no pathogenic Aβ arises. The molecular identity of α-secretase is similarly unknown.

α-Secretase is stimulated by acetylcholine, mediated by the muscarinic receptors m1 and m3 [Nitsch, R. M. et al.: Release of Alzheimer amyloid precursor derivatives stimulated by activation of muscarinic acetylcholine receptors. Science 258 (1992) 304–307]. The cellular mediator is protein kinase C ("PKC"). This is also confirmed by experiments which, following direct stimulation of PKC by phorbol ester, reach the same result [Buxbaum, J. D. et al.: Processing of Alzheimer beta/A4 amyloid precursor protein: Modulation by agents that regulate protein phosphorylation. Proc. Natl. Acad. Sci. USA 87 (1990) 6003–6006].

Tacrine, the most successful therapeutic agent to date against AD is an acetylcholine inhibitor [Giacobini, E.: Cholinomimetic therapy of Alzheimer disease: Does it slow down deterioration? In Recent Advances in the Treatment of Neurodegenerative Disorders and Cognitive Dysfunction, Int. Acad. Biomed. Drug Res. 7 (1994) 51–57. Racagni, G. et al., eds. Basel: Karger].

This may be interpreted as indirect stimulation of α-secretase by the following signal chain: Tacrine inhibits acetylcholinesterase. The concentration of acetylcholine is thereby increased. Acetylcholine activates the PKC via the muscarinic receptors m1 and m3. By this means the activity of α-secretase is increased. In consequence the quantity of pathogenic Aβ is lowered.

From these findings it can be concluded that selective activation of PKC can be an effective therapeutic starting point to inhibiting the production of amyloidogenic Aβ and thus to the treatment of AD. Since, of all 11 PKC isoenzymes, the γ-form is the only sub-type to be expressed exclusively in neuronal cells, substances which stimulate PKC-γ represent a new starting point to the therapy of AD. Moreover, all substances or processes which stimulate α-secretase or inhibit β- and γ-secretase are suitable for preventing the release of pathogenic Aβ and thus for treating the cause of AD.

STATE OF THE ART

The phloroglucin derivative hyperforin is one of the principal ingredients in fresh St. John's wort. It is associated with its homologue adhyperforin in a lower concentration. As both substances are highly unstable to light and the influence of air, their content declines even when the fresh plant is dried. By fast and careful drying followed by suitable extraction methods, extracts with a content of about 3–60% hyperforin/adhyperforin can be obtained [DE 19619512 C1].

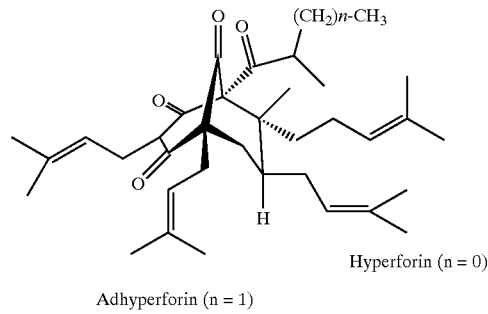

Adhyperforin (n = 1)

Hyperforin (n = 0)

However, without addition of appropriate stabilisers, hyperforin is not stable, and can therefore be obtained and stored in an enriched or pure form only by use of expensive techniques.

Reference has already been made to the importance of hyperforin for achieving the antidepressant efficacy of St. John's wort extracts in EP-A-0599307. Since then it has been scientifically proven that, on the basis of its pharmacological profile, hyperforin exerts a considerable influence in the medical treatment of depression and other serotonin-dependent diseases [S. S. Chatterjee et al., hyperforin and hypericum extract, Interactions with some Neurotransmitter Systems (SL-82), 2nd Intern. Congress on Phytomedicine, Sep. 11–14, 1996, Munich. See also: Pharmacopsychiatry 1998, 31 Suppl. I, 1–60].

Alzheimer's dementia (AD) is a serious disease of gradual onset which affects a considerable proportion of the population especially the elderly. It is characterised by initial forgetfulness, then increasing memory disturbances and losses of other cognitive abilities. It concludes with complete mental degeneration and loss of personality, and takes an ultimately fatal course. To date, no satisfactory, cause-orientated therapy for AD is available [K. Mendla, Die Alzheimer-Krankheit: Neue Ansätze in der Pharmakotherapie (1996). Pharm.Ztg. 141, 351–356].

TECHNICAL PROBLEM

The technical problem underlying the invention thus consists in the fact that, firstly, there is no known technically satisfactory method for obtaining and stabilising pure or greatly enriched hyperforin and adhyperforin, severely impeding the isolation, storage and use of these substances; secondly, there is a deficiency of active substances for the cause-orientated therapy of Alzheimer's disease, resulting in massive financial outlays within the social services. The problem of the invention is to help eliminate these defects.

SOLVING THE TECHNICAL PROBLEM

This problem is resolved according to the invention by the new salts of hyperforin and adhyperforin according to patent claims 1 to 5;

the method of manufacturing these salts according to Claim 6;

the method of enriching or purifying hyperforin and adhyperforin in the form of these salts according to Claims 7 and 8;

the use of these salts for maintaining stable stocks of hyperforin, adhyperforin and their mixtures according to Claim 9;

the pharmaceutical preparation according to Claim 10, and the new use of hyperforin, adhyperforin and their mixtures as medicinal products for the treatment of AD (2$^{nd}$ medical indication).

It was surprisingly found that the instability of hyperforin or of adhyperforin can be completely eliminated or at least considerably reduced by conversion of the substance into suitable salts of general formula I

(I)

No salts of hyperforin are known to date.

In formula I, m is a whole number from 1 to 3 and [A$^-$] is the anion of hyperforin or adhyperforin, where n=0 or 1 (general formula II):

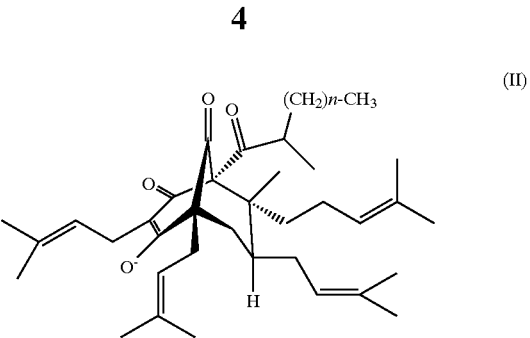
(II)

and [B]$^{p+}$ is either an ion of an alkali metal, preferably Li$^+$, Na$^+$ or K$^+$, where p=1, or an ammonium ion of a salt-forming nitrogen base of general formula III

(III)

wherein the residues R1, R2 and R3,
independently of one another, are a hydrogen atom, a straight-chain or branched alkyl, cycloalkyl, bicycloalkyl, tricycloalkyl, alkenyl, alkynyl, heterocycloalkyl, aryl, heteroaryl, arylalkyl or heteroarylalkyl group, or a derivative of the said groups substituted with one or more hydroxy, alkoxy, aryloxy, alkanoyl, aroyl, carboxy, alkoxycarbonyl, amino, alkylamino, hydroxylamino, amido, carbamoyl, ureido, amidino, guanidino, cyano, azido, mercapto, alkylthio, alkylsulphoxy, alkylsulphonyl, alkylsulphenyl, aminosulphonyl, fluoro, chloro, bromo, iodo, alkyl or perfluoroalkyl residue(s), or wherein the residues R1 and R2
together with the N atom are an azetidine, pyrrolidine, pyrroline, piperidine, piperazine, homopiperazine, morpholine, thiomorpholine, pyridine, di- or tetrahydropyridine, pyrimidine, pyrazine, azepine, dihydroazepine, oxazepine, diazepine, imidazole, pyrazole, oxazole, or thiazole ring, or one of the said rings which exhibits aliphatic, heteroaliphatic, aromatic or heteroaromatic rings condensed on to it and/or is substituted with one or more hydroxy, alkoxy, aryloxy, alkanoyl, aroyl, carboxy, alkoxycarbonyl, amino, alkylamino, hydroxylamino, amido, carbamoyl, ureido, amidino, guanidino, cyano, azido, mercapto, alkylthio, alkylsulphoxy, alkysulphonyl, alkylsulphenyl, aminosuiphonyl, fluoro, chloro, bromo, iodo, alkyl or perfluoroalkyl residue(s), and wherein the residue R4
is a hydrogen atom or a straight-chain or branched alkyl group, in which p=m and gives the total number of positive charges of the residue [B].

The N,N-dicyclohexylamine salts of hyperforin and adhyperforin and their mixtures are especially preferable.

From the above definition of the base B serving as a salt-former it emerges that a large number of basic compounds of nitrogen are suitable for satisfactorily increasing the stability of hyperforin or adhyperforin, both of which are unstable in the uncharged form.

Suitable bases are e.g.:

aliphatic and cycloaliphatic amines or polyamines such as mono-, di-, or tri-($C_3$ to $C_{20}$)alkylamines, aminoethanol, methylaminoethanol, dimethylaminoethanol, choline, 2-hydroxy-1,1-dimethylethylamine, tris(hydroxymethyl)methylamine, N-methyl-D-glucamine, ethylenediamine, dicylohexylamine, N-cyclohexyl-N-3-aminopropylamine, 1-aminoadamantane or 1-amino-3,5-dimethyladamantane, optionally substituted with one or more hydroxyl groups, cyclic or heterocyclic amines such as pyrrolidine, piperidine, morpholine, piperazine, N-methylpiperazine or N-methylhomopiperazine, optionally substituted with one or more lower alkyl- (=$C_1$ to $C_4$-alkyl) or hydroxyl residues, possibly substituted aromatic, heteroaromatic, arylaliphatic or heteroarylaliphatic amines such as benzylamine, 3,4,5-trimethoxybenzylamine, veratrylamine, phenethylamine, homoveratrylamine, N-methylhomoveratrylamine, 4-aminopyridine, tacrine and analogues, imipramine, desipramine, selegiline, nicotine, pindolol, amino acid esters and amides such as methyl, ethyl, propyl or isopropyl esters and amides of glycine, alanine, phenylalanine, leucine, isoleucine, methionine, proline, valine, sarcosine, pipecolic acid, as well as basic amino acids such as lysine or arginine or their amides.

Bases which are especially suitable are those that are themselves active substances and have the same medical indications as hyperforin, or support its therapeutic use. Those coming into consideration are primarily basic active substances with the indications:

Alzheimer's Disease (AD), e.g.
  Acetylcholinesterase inhibitors (e.g. amiridine, donezepil, ensaculine, eptastigmine, galanthamine, huperzine A, 7-methoxytacrine, physostigmine, SDZ-ENA-713 (Exelon), SM-10888, suronacrine, tacrine, velnacrine), cholinergic activators, NMDA antagonists (e.g. memantine), glutamine-receptor antagonists, serotonin agonists and antagonists (e.g. adatanserin), monoamine oxidase inhibitors (e.g. tranylcypromine, selegelin), PKC activators and α-secretase inhibitors, tyrosine kinase antagonists, muscarinic agonists (e.g. arecoline, BIBN 99, itameline, milameline, talsaclidine, xanomeline, YM796), Antidepressants, e.g.
  amitryptiline, dibenzepin, desipramine, desitryptiline, doselupine, doxepin, clomipramine, fluoxetine, fluvoxamine, imipramine, lofepramine, maprotiline, moclebemide, mianserin, nortriptyline, opipramol, paroxetine, tranylcypromine, trazodone, trimipramine, viloxazine, Anxiolytics, e.g.
  chlorprothixene, dixyrazine, fluphenazine, levomepromazine, melperone, perphenazine, promazine, promethazine, pritiphendyl, sulpiride, tandospirone, thioridazine, trifluoperazine, zuclopenthixol, Calcium antagonists (with basic side chain) e.g.
  amlodipine, azelnidipine, bamidipine, benidipine, cronidipine, edrecolomab (AE0047), efonidipine, elgodipine, lercanidipine, manidipine, nicardipine, palodipine, verapamil, Dyspepsia therapeutic agents and prokinetics, e.g.
  cisapride, metoclopramide, renzapride (5-$HT_4$ agonists), β-receptor blockers, e.g.
  atenolol, alprenolol, carazolol, propranolol, labetalol, mepindolol, metoprolol, oxprenolol, penbutolol, pindolol, bupranolol, bunitrolol, metipranolol, nadolol, Nootropics, e.g.
  lomerizine, nebracetam, pramiracetam, SNK-882.

Salts of hyperforin and adhyperforin with basic active substances of this type form an especially innovative partial aspect of the present invention, as they not only increase the stability of the therapeutically active hyperforin, but also, in consequence of their intrinsic therapeutic action, allow an especially appropriate combination of mutually potentiating or mutually supporting active principles.

MANUFACTURE OF THE SALTS ACCORDING TO THE INVENTION

The salts according to the invention can be manufactured in various ways. In the following explanation of the method, the term "hyperforin" in all cases also means the homologue adhyperforin and mixtures of the two substances. "Lower" always means "$C_1$ to $C_4$-".

Method A: Hyperforin is dissolved in a lower alkanol (e.g. methanol, ethanol, propanol or isopropanol), preferably under protective gas and with exclusion of light, reacted with the solution of an equimolar quantity of alkali-metal hydroxide or alkali-metal lower alkoxide (e.g. sodium methoxide or ethoxide) in one of the above-mentioned lower alkanols, the solution is evaporated, taken up with water and lyophilised. Stable, colourless to cream-coloured alkali salts of hyperforin are obtained in the form of a powder. Alternatively the hyperforin can also be dissolved directly in the solution of the alkali metal lower alkoxide and worked up as above.

Method B: Hyperforin is dissolved in an aprotic solvent selected from the group of apolar $C_1$–$C_{10}$ alkanes and $C_1$–$C_{10}$ cycloalkanes e.g. pentane, hexane, heptane, octane, isooctane, or cyclohexane, optionally with addition of small quantities of a lower alkanol (e.g. methanol, ethanol, or isopropanol), preferably under protective gas and with exclusion of light, this solution is reacted with the equimolar quantity of the basic component B or with a solution of the same in one of the above-mentioned solvents or in a lower halogenoalkane, e.g. dichloromethane or chloroform, or in a lower ether, e.g. diethyl ether, diisopropyl ether, tert.-butyl methyl ether or tetrahydrofuran, or in a lower ketone, e.g. acetone or methyl ethyl ketone, the mixture concentrated if necessary, the precipitating salt separated, if necessary recrystallised, and dried under vacuum. Crystalline or amorphous ammonium salts of hyperforin are obtained in the form of a powder.

If the base B contains more than one basic centre capable of salt formation, if desired correspondingly smaller quantities, e.g. ½ or ⅓-molar quantities of base B may be used, so that the hyperforin/base ratio is m/p.

Method C: Hyperforin is dissolved in a lower alkanol (e.g. methanol, ethanol, or isopropanol), preferably under protective gas and with exclusion of light, this solution is reacted with the equimolar quantity of the basic component B or with a solution of the same in one of the above-mentioned solvents, the mixture is evaporated, taken up in water, and lyophilised. Crystalline or amorphous ammonium salts of hyperforin are obtained in the form of a powder.

Method D: Hyperforin is dissolved in a lower alkanol (e.g. methanol, ethanol, or isopropanol), preferably under protective gas and with exclusion of light, this solution is reacted with an equimolar quantity of the basic component B in water, the lower alcohol is removed by distillation under vacuum, and the remaining aqueous mixture is lyophilised, if necessary after addition of water. The powdery salt obtained is if necessary re-crystallised from a lower alcohol, alcohol/water mixture or from a lower ester.

Method for the Enrichment or Pure Isolation of Hyperforin and Adhyperforin From St.-John's Wort Extracts To date the purification of hyperforin from St.-John's wort extract has been possible only with the use of very expensive chromatographic methods which were furthermore made technically unacceptable by the high instability of hyperforin and its homologue to light and to the oxygen in air (P. Maisenbacher, Universität Tübingen, Diss. 1991. R. Burgdörfer, Universität Marburg, Diss. 1987).

A surprisingly simple and cost-reducing solution to this technical problem has now been found which consists in dissolving St.-John's wort extracts, e.g. a $CO_2$ extract with a 20–80% hyperforin/adhyperforin content, in a suitable solvent selected from the series of apolar $C_1$–$C_{10}$ alkanes and cycloalkanes, e.g. pentane, hexane, heptane, octane, iso-octane, or cyclohexane, optionally with addition of small quantities of a lower alkanol (e.g. methanol, ethanol or isopropanol), preferably under protective gas and with exclusion of light, this solution is reacted with the at least equimolar quantity of the basic component B or a solution of the same in one of the above-mentioned solvents or in a lower halogenoalkane, e.g. dichloromethane or chloroform, or in a lower ether e.g. diethyl ether, diisopropyl ether, tert.-butylmethyl ether or tetrahydrofuran, or in a lower ketone, e.g. acetone or methyl ethyl ketone, the mixture is concentrated if necessary, the precipitating salt is separated, if necessary re-precipitated and/or re-crystallised and dried under vacuum. Crystalline or amorphous ammonium salts of hyperforin/adhyperforin or of a mixture of them are obtained in the form of a powder.

Salt-forming amines especially suitable for this method are cycloaliphatic (e.g. dicyclohexylamine) araliphatic (e.g. benzylamine and its methoxy-substituted derivatives), heterocyclic or heteroaromatic amines (e.g. 4-aminopyridine).

Hyperforin/adhyperforin can be readily obtained in a pure form from the crystalline and storage-stable salts by acidification, preferably with an organic acid (e.g. citric acid or tartaric acid), and subsequent distribution between one of the listed solvents and water, and either used as they are or transferred to other desired salts. To this end the hyperforin salt is dissolved or suspended in the selected solvent (e.g. methyl-tert.butyl ether or ethyl acetate), under a protective-gas atmosphere and exclusion of light, reacted with the at least equimolar quantity of the acid dissolved in water, stirred until completely dissolved, the aqueous phase is separated, and the organic phase is evaporated gently after washing with water.

Medicinal Products

The present invention further relates to medicinal products which, in addition to non-toxic, inert pharmaceutically suitable carrier substances, also contain one or more of the hyperforin and/or adhyperforin salts according to the invention, or which consist of one or more of the hyperforin and/or adhyperforin salts, as well as methods of manufacturing these medicinal products.

Non-toxic, inert pharmaceutically suitable carrier substances are to be understood as solid, semi-solid or liquid diluents, fillers and formulation adjuvants of all kinds.

Suitable solid or liquid galenical preparations of the medicinal products according to the invention are e.g. tablets, capsules, sugar-coated tablets, suppositories, syrups, emulsions, suspensions, drops or injectable solutions, as well as products with slow release of the active substance.

As carriers or diluents one should name e.g. various sugars or starches, cellulose derivatives, magnesium carbonate, gelatins, oils of animal or vegetable origin, polyethylene glycols, water or other physiologically safe solvents, as well as water-containing buffers, which may be rendered isotonic by addition of salts or glucose. Surfactant substances, colourings, flavourings, stabilisers and preservatives may also find a use as further additives in the medicinal products according to the invention.

The therapeutically effective compounds are present in the medicinal products listed above preferably in a concentration of about 0.5 to 95% of the overall mixture.

The medicinal products are manufactured using methods familiar to the person skilled in the art, e.g. by mixing of the active substance(s) with the carrier substances and additives and further processing to produce the desired galenical form.

The invention also relates to the use of the active substances of the invention, and of the medicinal products manufactured from them, in human medicine for the therapy or prophylaxis of Alzheimer's disease.

Finally, the invention relates to the use of the substances hyperforin and/or adhyperforin, known ingredients of extracts used for therapeutic purposes, if necessary together with a pharmaceutically safe carrier or diluent, in human medicine for the therapy or prophylaxis of Alzheimer's disease (2nd medical indication)

The active substances or medicinal products of the invention may be administered orally, parenterally, intravenously and/or rectally. In human medicine, the active substances are preferably administered in doses amounting in total to 0.01 to 10, in particular 0.05 to 5 mg/kg body weight per 24-h period, if necessary in the form of several unit doses. The total amount is administered in 1 to 5, preferably in 1 to 3 unit doses. The dosage and timing of the doses, and the choice of appropriate mode of administration can easily be accomplished by anyone skilled in the art on the basis of his or her scientific knowledge.

The following examples are intended to illustrate the invention without limiting its scope.

General: Melting points were measured with Elektrothermal® or B-545 (Büchi) apparatus; IR spectra were recorded with an IFS 28 (Bruker) IR-spectrometer on KBr blanks, NMR spectra with an AC 200 or Avance 200 (Bruker) in $D_4$-methanol (200 MHz for $^1H$ and 50 MHz for $^{13}C$; δ-values in ppm). HPLC determinations were performed using a Dynamax PDA-1 from Rainin, Voburn, Mass., USA. HPLC conditions (isocratic): adsorbant: Eurospher 100-C18, 10 μm. Eluant: Acetonitrile/water/phosphoric acid=85/15/0.3 (vol./vol.). Detection: 273 nm. Reference standard: Hyperforin dicyclohexylamine salt according to example 2b=100%. Assay: Content stated in area-% with reference to the reference standard. Stated contents of hyperforin (adhyperforin) in their salts are in all cases given as a percentage of the stoichiometric proportion of hyperforin (adhyperforin). Solvent: Methanol (p.a. or ultra pure), methyl-tert.butyl ether (>99%), isopropanol (>99%) and water (bidistilled) are degassed prior to use. Operating conditions: under red light or in darkened apparatus under protective gas (nitrogen or argon). Elementary analysis: lyophilised products occasionally contain residual water. They are calculated as hydrates. Abbreviations: MTBE=Methyl tert.-butyl ether. "98H/I"=n-heptane/isopropanol 98/2 (vol/vol). Mp.=melting point. anh.=anhydrous. Th=theoretical. sv=very strong.

EXAMPLE NO. 1a
Method A

Hyperforin Sodium Salt.

23 mg (1 mmol) sodium is dissolved in 50 ml anhydrous methanol. 536 mg (1 mmol) hyperforin is dissolved in this solution under stirring, and the solution evaporated. The residue is dissolved in 100 ml water and lyophilised. Yield: 556 mg of a light-coloured powder (99.6% of theoretical). Mp.: Degradation from 170° C. IR: 1420–1500 cm$^-$(sv).

EXAMPLE NO. 1b
Method A

Hyperforin Sodium Salt.

728.5 mg (1.31 mmol) 96.5% hyperforin is dissolved in 80 ml methanol, reacted with 5.1 ml (1.32 mmol) 0.259-molar methanolic sodium hydroxide solution, allowed to stand for a short time, and the solution evaporated at 50° C. The residue is dissolved in water and lyophilised. Yield: 746.7 mg of a white powder (101% of theoretical). Mp.: Sintering between 90° C. and 110° C., degradation at 170° C. IR: 1449 cm$^{-1}$ (sv, broad). $^1$H-NMR: no impurities apart from approx. 1.4 mol % (0.08 weight-%) methanol visible. $C_{35}H_{51}NaO_4$ (558.78). Calculated/recovered: C (75.23/71.61), H (9.20/8.87); Na (4.11/4.6). Hyperforin content (HPLC): 86.5%.

EXAMPLE NO. 2a
Method B

N,N-Dicyclohexylamine Salt of Hyperforin.

1 g (1.86 mmol) hyperforin is dissolved in 50 ml n-pentane/methanol 98/2 vol/vol, reacted with 445 µl (2.33 mmol) dicyclohexylamine and allowed to stand for 10 h at 4° C. Precipitated product is drawn off by suction over a sintered glass filter, washed with pentane and dried under vacuum at room temperature. Yield: 652 mg of a white powder (48.7% of theoretical). Mp.: 157.2° C. IR: 1473, 1489 cm$^{-1}$ (sv). $C_{47}H_{75}NaO_4$ (718.13). Calculated/recovered: C (78.61/76.91), H (10.53/10.42); Na (1.95/1.70). NMR: In addition to the signals of hyperforin, the following signals of dicyclohexylamine are visible: $^1$H-NMR: 3.15 (m; 2 H; 1-CH) and (partially overlapping) 1.82–2.08 (m, 2- and 6-CH$_2$), 1.42 (quint, 3-, 4-, and 5-CH$_2$). Dicyclohexylamine/hyperforin quotient=1/1. No visible impurities. $^{13}$C-NMR: 54.65 (1-CH), 30.72 (2- and 6-CH$_2$, 26.06 (4-CH$_2$) and 25.64 (3- and 5-CH$_2$) The substance is recrystallised from pentane/methanol. Mp.: 163.9° C. $C_{47}H_{75}NO_4$ (718.13). Calculated/recovered: C (78.61/78.92), H (10.53/10.44); N (1.95/1.79). Hyperforin content (HPLC): 1 00%.

EXAMPLE NO. 2b
Method B

N,N-dicyclohexylamine Salt of hyperforin.

1.547 g (2.82 mmol) 98% hyperforin is dissolved in 60 ml n-heptane/isopropanol 98/2 vol/vol, reacted with 600 µl (3.0 mmol) dicyclohexylarnine and allowed to stand for 18 h under N$_2$ at room temperature. Precipitated product is drawn off by suction over a sintered glass filter, washed with heptane and dried under vacuum at room temperature for 8 h. Yield: 1.767 g (2.46 mmol) of a white powder (87% of theoretical). Mp.: 159.7° C. IR: 1473, 1489 cm$^{-1}$ (sv).

$^1$H-NMR: corresponds to the $^1$H-NMR spectrum of example 2a. $C_{47}H_{75}NO4$ (718.13). Calculated/recovered: C (78.61/78.59), H (10.53/10.66); N (1.95/1.87). Hyperforin content (titration with HClO$_4$): 100%.

EXAMPLE NO. 3a
Method B 3,4,5-Trimethoxybenzylamine Salt of Hyperforin.

57.8 mg (0.1 mmol) 93.5% hyperforin is dissolved in 2 ml n-pentane and immediately reacted with 50 µl of a 2M solution of 3,4,5-trimethoxybenzylamine in MTBE. The colourless precipitate is drawn off by suction, washed with pentane and dried under vacuum at room temperature. Yield: 10 mg of a white crystallisate (14% of theoretical). IR: 1480 cm$^{-1}$ (sv). $C_{47}H_{67}NO_7$ (734.04).

EXAMPLE NO. 3b
Method C 3,4,5-Trimethoxybenzylamine Salt of Hyperforin.

58.3 mg (0.1 mmol) 92.7% hyperforin is dissolved in 2 ml anhydrous methanol, reacted with 19.7 mg (0.1 mmol) freshly distilled 3,4,5-trimethoxybenzylamine, diluted with 2 ml methanol and evaporated at 50° C. The evaporate is taken up in 20 ml water and lyophilised. Yield: 70.4 mg of a white powder (96% of theoretical). Mp.: 126–33° C. IR: 1484 cm$^{-1}$ (sv). $C_{45}H_{67}NO_7$ (734.04). Hyperforin content: (HPLC): 87.2%.

EXAMPLE NO. 4
Method D

L-arginine Salt of Hyperforin.

58.3 mg (0.1 mmol) 92.7% hyperforin is dissolved in 2 ml anhydrous methanol, reacted with the solution of 17.4 mg (0.1 mmol) L-arginine in 0.5 ml bidist. water and 15 ml methanol, and concentrated under vacuum at 50° C. The residue is diluted with 10 ml water and lyophilised. Yield: 58.1 mg of a white powder (81.7% of theoretical). Mp.: Sintering from 110° C., degradation at 145° C. IR: 1486 cm.$^{-1}$ (sv). $C_{41}H_{66}NO6$ (711.01). Hyperforin content: (HPLC): 82.7%.

EXAMPLE NO. 5
Method B

Pyrrolidine Salt of Hyperforin.

578 mg (1.0 mmol) 93.5% hyperforin is dissolved in 15 ml n-pentane, then reacted with 85 µl (1.0 mmol) pyrrolidine, and allowed to stand for 24 h at room temperature (no crystallisation) and 24 h at −20° C. (oily precipitation of the product). The mixture is evaporated, the evaporate dissolved in water/methanol, and lyophilised. Yield: 576 mg (0.947 mmol) of a colourless powder (94.7% of theoretical). IR: 1489 cm$^{-1}$ (sv). $C_{39}H_{61}NO_4$ (607.93). Hyperforin content: (HPLC): 93.7%.

EXAMPLE NO. 6
Method D

Ethylene Diamine Salt with 2 Mol Hyperforin.

58.3 mg (0.1 mmol) 92.7% hyperforin is dissolved in 2 ml methanol, reacted with 50 µl of a 1M solution of ethylene diamine in water and 2 ml methanol, and concentrated under vacuum at 50° C. The residue is diluted with 20 ml water, and lyophilised. Yield: 57.1 mg of a white powder (100.7% of theoretical). Mp.: (sintering from 40° C.) 50–2° C. IR: 1480 cm$^{-1}$ (sv). $C_{72}H_{112}N_2O_8$(1133.70). Hyperforin content: (HPLC): 83.1%.

EXAMPLES NOS. 7 to 20

Further examples of hyperforin salts in accordance with the invention are presented in Table 1 below. After lyophilisation the salts are present as colourless or cream-coloured powders. Their composition is confirmed by NMR- and IR-spectroscopy.

TABLE No. 1
| No. | Structure | Salt-former | Method | Yield [%] | Melting range [° C.] | IR [cm⁻¹] | Hyperforin content HPLC [% th.] |
|---|---|---|---|---|---|---|---|
| 7 | 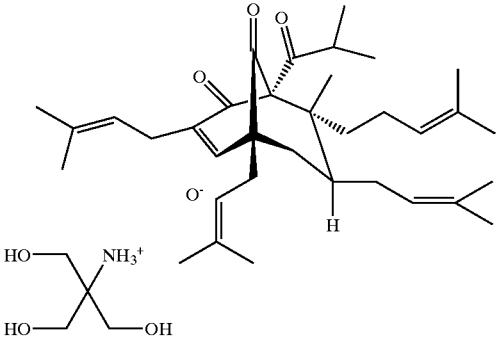 | Tris-(hydroxy-methyl)-aminomethane | D | 88 | 37–53 | 1489 sv | 90.4 |
| 8 | 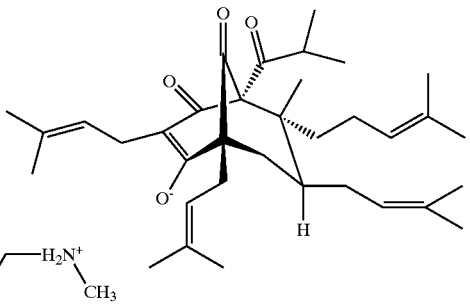 | 2-methyl-aminomethanol | D | 101 | 42–50 | 1491 sv | 85.3 |
| 9 | 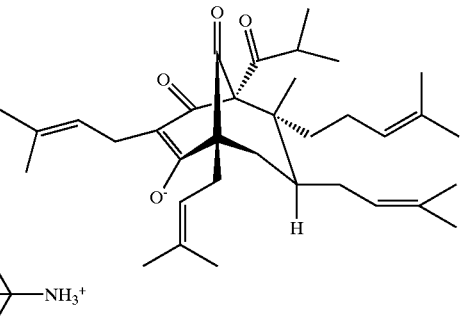 | 2-amino-2-methylpropanol | D | 100 | 72–5 | 1487 sv | 86.1 |
| 10 | 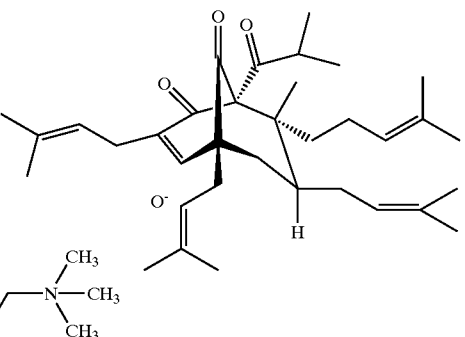 | Chloline | C | 100 | 58–61 | 1505 sv | 78.7 |

TABLE No. 1-continued

| No. | Structure | Salt-former | Method | Yield [%] | Melting range [° C.] | IR [cm$^{-1}$] | Hyperforin content HPLC [% th.] |
|---|---|---|---|---|---|---|---|
| 11 | 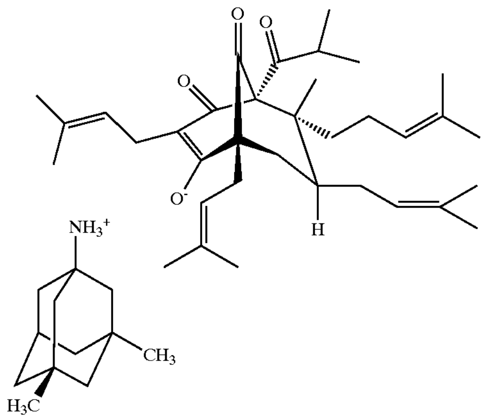 | 1-amino-3,5-dimethyl-adamantane (Memantin) | C | 100 | 62–70 | 1487 sv | 88.8 |
| 12 | 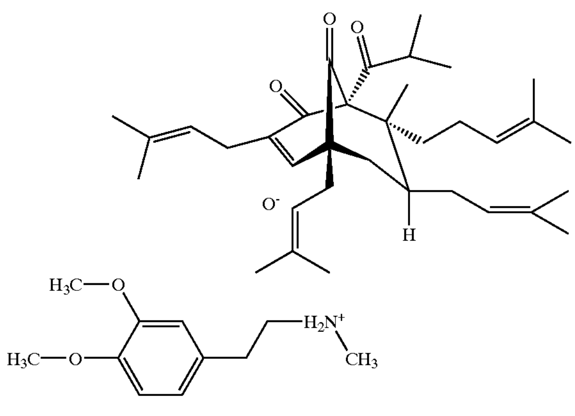 | N-methyl-homoveratryl-amine | C | 100 | 47–57 | 1491 sv | 75.0 |
| 13 | 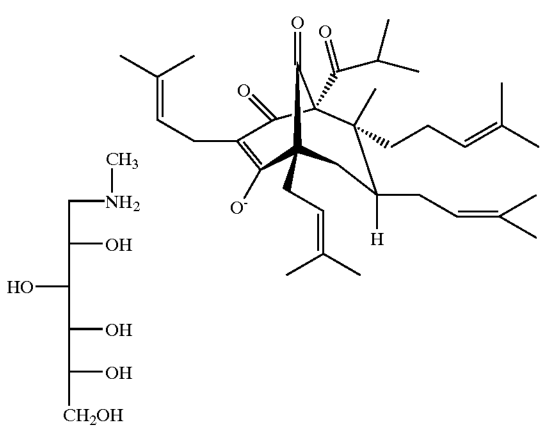 | N-methyl-D-glucamine (Meglumin) | D | 100 | 48–68 | 1493 s | 76.4 |

TABLE No. 1-continued

| No. | Structure | Salt-former | Method | Yield [%] | Melting range [° C.] | IR [cm⁻¹] | Hyperforin content HPLC [% th.] |
|---|---|---|---|---|---|---|---|
| 14 | 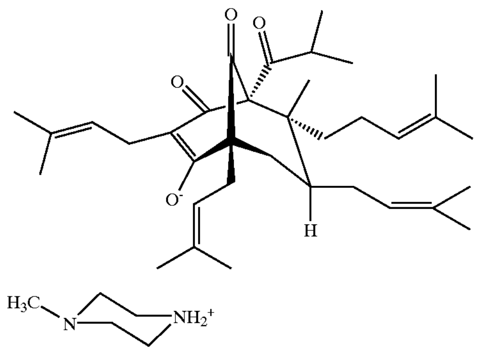 | 1-methyl-piperazine | D | 95 | 57–62 | 1491 sv | 92.9 |
| 15 | 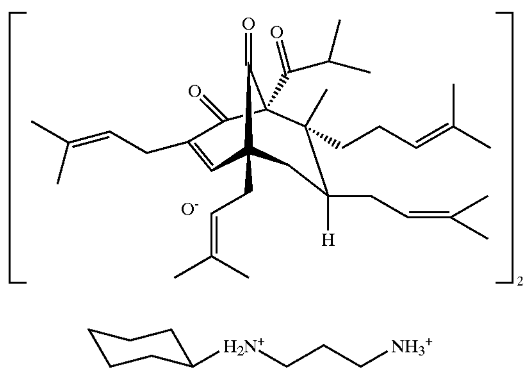 | N-(3-amino-propyl)-N-cyclo-hexylamine (APCHA) | D | 100 | 55–8 | 1486 sv | 90.8 |
| 16 | 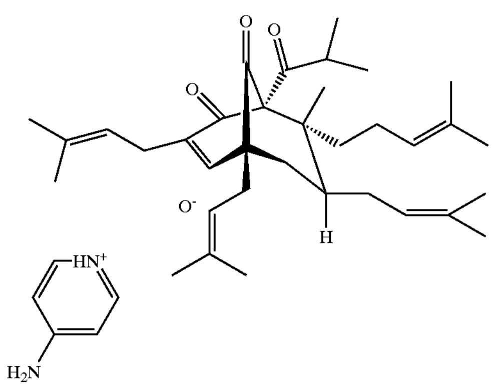 | 4-amino-pyridine | D | 92.7 | 80–2 | 1486 sv | 94.6 |
| 17 | 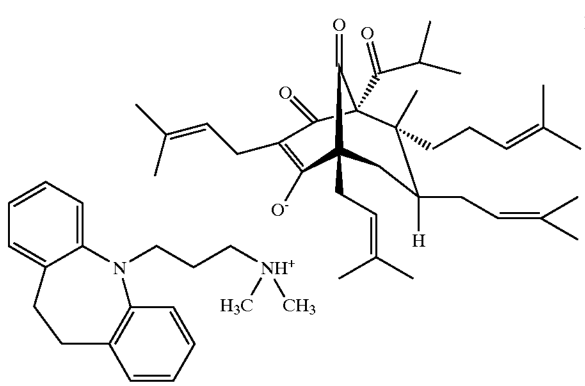 | Imipramine | C | 100 | 45–60 | 1489 s, 1500 s | 90.5 |

TABLE No. 1-continued

| No. | Structure | Salt-former | Method | Yield [%] | Melting range [° C.] | IR [cm$^{-1}$] | Hyperforin content HPLC [% th.] |
|---|---|---|---|---|---|---|---|
| 18 | 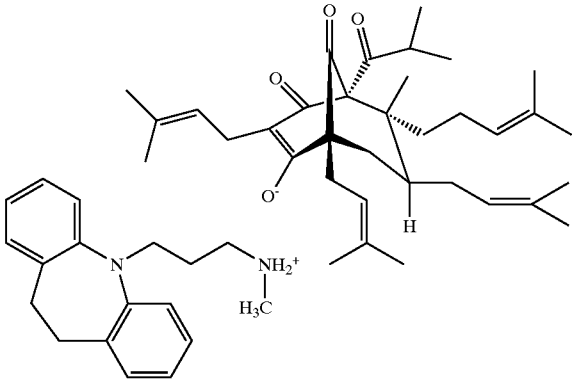 | Desipramine | C | 100 | 69–75 | 1489 ss | 90.9 |
| 19 | 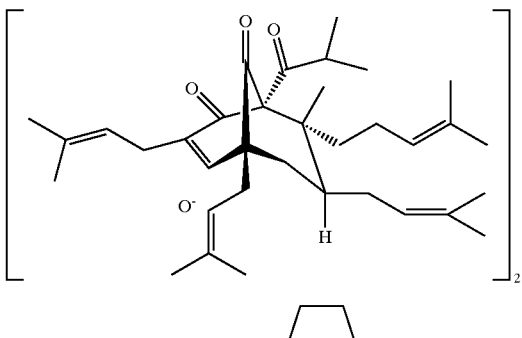 | Nicotine | D | 97.5 | 48–50 | 1492 s | 94.9 |
| 20 | 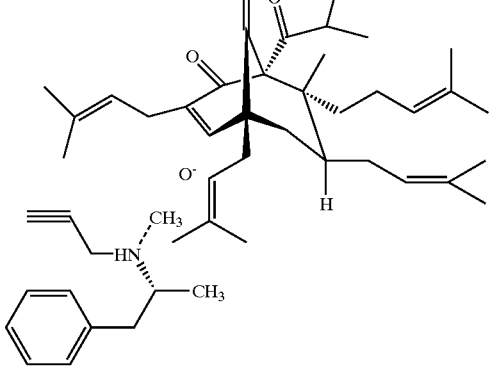 | Selegelin (Deprenyl) | C | 74 | 37–47 | 1495 m | 110.2 |

EXAMPLE NO. 21

Isolation of hyperforin/adhyperforin from a hypericum-CO$_2$ extract content: 32.1% hyperforin, 6.8% adhyperforin) by precipitation as N,N-dicyclohexylamine salt and recrystallisation.

a) 200 g of the extract (145 mmol hyperforin+adhyperforin) is extracted with 2.8 L n-heptane/isopropanol 98/2 ("98H/I") in a rotating flask at 40°C., 200 g anhydrous sodium sulphate is added, stirred for 30 min, filtered from the undissolved material (Super Seitz 1500 filter plate) and washed with 200 ml "98H/I". 29 g (160 mmol) dicyclohexylamine is added dropwise to the filtrate under stirring, and the mixture is allowed to stand for 16 h at 20° C.

The crystallisate is drawn off by suction, washed with "98H/I" and dried under vacuum (K1: 55.76 g). The mother liquor is concentrated to ⅓ of the volume, stored for 16 h at 20° C. and cooled to 4° C. The supernatant is decanted from the crystallisate, and the crystallisate is washed with "98H/I" and dried (K2: 37.95 g).

The raw crystallisate (K1+K2: 93.71 g; HPLC content: 67.2% hyperforin, 14.1% adhyperforin) is dissolved in 400 ml (ultra pure) methanol, stored for 4h at 4° C., precipitated waxy material is drawn off by suction, the filtrate is concentrated, dissolved in 200 ml MTBE, 300 ml n-pentane added, stored for 16 h at 20° C. and cooled to 4° C. The crystallisate is drawn off by suction, washed 2× with cold MTBE/pentane, pre-dried under vacuum (approx. 20 hPa), and dried at 60° C./0.1 hPa [46.73 g K3; Mp.: 161.6–162.0° C. HPLC content: 84.9% hyperforin, 17.5% adhyperforin]. The mother liquor is concentrated to 2/3 of the volume, stored as above, the crystallisate is drawn off by suction, washed and dried as above [30.92 g K4]; Mp.: 158.8–159.2° C. HPLC content: 78.9% hyperforin, 19.2% adhyperforin].

Total yield: 77.29 g dicyclohexylamine salt of hyperforin/adhyperforin (approx. 82/18)=approx. 74%.

b) 1000 g of the extract (725 mmol hyperforin+adhyperforin) is dispersed in 15 L methanol for 15 min at 22–29° C. with an Ultra-Turax, stored for 17 h at 4° C., and precipitated wax is filtered off through a Seitz-Supra 2600 single-layer filter. The filter cake is washed with 1 l methanol, and the combined filtrates concentrated to approx. 1/3 of the volume. The concentrate, cooled to 20° C., is saturated with heptane, extracted with 3×2 l methanol-saturated heptane, and the combined extracts re-extracted with 2×500 ml heptane-saturated methanol. The combined methanol extracts are evaporated at 40° C., thereafter dissolved in 8 l "98H/I" at 40° C. under rotation, cooled to 20° C., reacted with 159 ml (798 mmol) dicyclohexylamine under stirring, protection from light, and argon, and the immediately crystallising mixture is stored for 16 h at 4° C. The crystallisate is drawn off by suction, washed with "98H/I" and dried under vacuum. The dry product (425 g) is suspended in 1.5 l MTBE, stirred for 5 min at 40° C., the crystallisate drawn off by suction after cooling to 20° C., washed with cold MTBE, and dried for 24 h at 20° C./10 hPa. Yield: 355.0 g (494 mmol)=68.2%. Mp.: 161.0° C. HPLC content: 82.44% hyperforin, 17.39% adhyperforin, together 99.83%.

EXAMPLE NO. 22

Salt of Adhyperforin with Dicyclohexylamine.

The adhyperforin is isolated from a portion of the hyperforin/adhyperforin dicyclohexylamine salt (K4 in example 21) by preparative HPLC on RP-18 adsorbent (HPLC content: 93.8%). 34 mg (62 μmol) of this is dissolved in 2 ml "98H/I" under $N_2$ and exclusion of light, 12.5 μl (63 μmol) dicyclohexylamine is added by doping, after 18 h the crystallisate is drawn off by suction, washed with cold "98H/I" and dried for 18 h under vacuum. Yield: 12.5 mg (17 μmol)=27%. HPLC content: 91.2% adhyperforin.

EXAMPLE NO. 23

Release of Hyperforin/Adhyperforin From a Dicyclohexylamine Salt of Hyperforin/Adhyperforin (HPLC Content: 86% Hyperforin, 15% Adhyperforin).

A suspension of 718 mg (1.0 mmol) hyperforin/adhyperforin dicyclohexylamine salt in 60 ml MTBE is prepared, 10 ml 1-molar aqueous citric acid is added, stirred for 30 min, the MTBE phase is separated off, washed 3× with water, dried over sodium sulphate and evaporated. The colour-less oil is dried at 20° C./0.1 hPa. Yield: 527.6 mg (0.983 mmol)=98.3%. HPLC content: 86.8% hyperforin, 14.9% adhyperforin.

EXAMPLE NO. 24

Potassium Salt of Hyperforin/Adhyperforin.

537 mg (1.0 mmol) of a hyperforin/adhyperforin -9/1-mixture is dissolved in 100 ml methanol, reacted with 10 ml 0.1M-KOH in methanol, and evaporated. The residue is taken up in 80 ml water and lyophilised. Yield: 590.6 mg (99.6 mmol)=99.6% of a colourless powder. Mp.: 110–112° C. (sintering). HPLC content: 78.7% hyperforin, 8.8% adhyperforin. IR: 1499.5 $cm^{-1}$ (sv). $C_{35}H_{51}KO_4 \times H_2O$ (592.91).

EXAMPLE NO. 25

Lithium Salt of Hyperforin/Adhyperforin.

2.68 g (5.0 mmol) of hyperforin/adhyperforin -5/1- mixture is dissolved in 50 ml methanol, reacted with the solution of 0.210 (5.0 mmol) lithium hydroxide hydrate in 20 ml methanol, the mixture evaporated at 40° C., the residue dissolved in 30 ml water and lyophilised. Yield: 2.735 g (4.88 mmol)=97.5% of a colourless powder. Melting range: 80–93° C. HPLC content: 80.2% hyperforin, 15.0% adhyperforin; together 95.2%. IR: 1493.1 $cm^{-1}$ (sv). $C_{35}H_{51}LiO_4 \times H_2O$ (560.74).

EXAMPLE NO. 26

L-lysine Salt of Hyperforin/Adhyperforin.

2.68 g (5.0 mmol) of hyperforin/adhyperforin -5/1- mixture is dissolved in 50 ml methanol, reacted with the solution of 0.731 g (5.0 mmol) L-lysine in 10 ml water, and the clear mixture evaporated at 40° C. The residue is lyophilised after addition of 50 ml water. Yield: 3.35 g (4.78 mmol)=95.6% of a colourless powder. Melting range: 74–98° C. HPLC content: 83.25% hyperforin, 16.98% adhyperforin; together 100.2%. IR: 1483 $cm^{-1}$ (sv). $C_{41}H_{66}N_2O_6 \times H_2O$ (701.07).

EXAMPLE NO. 27

Pindolol Salt of Hyperforin/Adhyperforin.

2.68 g (5.0 mmol) of hyperforin/adhyperforin -8/1- mixture and 1.24 g (5.0 mmol) pindolol are dissolved in 50 ml methanol and evaporated at 40° C. The residue is lyophilised after addition of 50 ml water. Yield: 4.03 g (5.1 mmol)= 102% of a white foam. Melting range: 65–75° C. HPLC content: 91.2% hyperforin, 11.7% adhyperforin; together 102.9%. $C_{49}H_{72}N_2O_6$ (701.07).

EXAMPLE NO. 28

Pyrrolidine Salt of Hyperforin/Adhyperforin.

531 mg (0.99 mmol) of hyperforin/adhyperforin -5/1-mixture is dissolved in 10 ml methanol under exclusion of light, then reacted with 83.5 μl (0.98 mmol) pyrrolidine and concentrated on a rotary evaporator. The concentrate is taken up in 70 ml water and lyophilised. Yield: 570.6 mg (0.938 mmol)=95%. Melting range: 50–70° C. HPLC content: 79.5% hyperforin, 16.4% adhyperforin; together 95.9%. IR: 1489 $cm^{-1}$ (sv). $C_{39}H_{61}NO_4$ (607.93).

EXAMPLE NO. 29

Desipramine Salt of Hyperforin/Adhyperforin.

2.68 g (5.0 mmol) of hyperforin/adhyperforin -5/1- mixture is dissolved in 9/1 MTBE/pentane by warming under $N_2$ and exclusion of light under addition of a few drops of methanol, and then crystallised at −20° C. The crystallisate is drawn off by suction, washed with ice-cold 9/1 pentane/MTBE, and dried at RT/0.1 hPa. Yield: 4.03 g (5.0 mmol)= 100% of a white crystalline powder. Mp.: 154.8–155.3° C. HPLC content: 82.4% hyperforin, 16.3% adhyperforin; together 98.7%. IR: 1489 $cm^{-1}$ (sv). $C_{53}H_{74}N_2O_4$ (803.19).

EXAMPLE NO. 30

Hyperforin/Adhyperforin Sodium Salt.

5.94 g (11.1 mmol) of hyperforin/adhyperforin -9/1- mixture is dissolved in 50 ml methanol under $N_2$ and exclusion of light, reacted with 10.7 ml 1M-NaOH, and the methanol drawn off in a rotary evaporator at 40° C. under vacuum. The residue is taken up with 50 ml water and lyophilised. Yield: 6.2 g (11.1 mmol)=97.2% of a white powder. Melting range: 109–128° C. HPLC content: 91.3% hyperforin, 9.5% adhyperforin; together 100.8% of the theoretical value. IR: 1499 $cm^{-1}$ (sv). $C_{35}H_{51}NaO_4 \times H_2O$ (576.80).

EXAMPLE NO. 31

L-arginine Salt of Hyperforin/Adhyperforin.

2.68 g (5.0 mmol) of hyperforin/adhyperforin -5/1- mixture is dissolved in 50 ml methanol under $N_2$ and exclusion of light, reacted with the solution of 0.87 g (5.0 mmol) L-arginine in 10 ml water, and concentrated under vacuum at 50° C. The residue is diluted with 50 ml water and lyophilised. Yield: 3.59 g (4.92 mmol)=98.5% of a white powder. Melting range: 115–133° C. IR: 1486 $cm^{-1}$ (sv). HPLC content: 82.6% hyperforin, 17.0% adhyperforin; together 99.6%. $C_{41}H_{66}NO_6 \times H_2O$ (729.02).

EXAMPLE NO. 32

Stability of Hyperforin Salts.

Samples of hyperforin salts are stored in brown-glass bottles with snap-on caps at room temperature without protective gas, and the hyperforin (examples 1 to 20) or hyperforin+adhyperforin (examples 21 to 31) content is determined by HPLC (area%/o) at the storage times 0, 1 week, 4 weeks and 12 weeks. The changes in the hyperforin (+adhyperforin) content are presented in Table II.

TABLE II

Stability of hyperforin salts

| Substance according to Example No. | Initial value [%] | Difference after 1 week [%] | Difference after 4 weeks [%] | Difference after 12 weeks [%] | Comments |
|---|---|---|---|---|---|
| 1 | 85.9 | | −0.4 | −2.3 | |
| 2 | 100 (titr.)[1] | ±0.0 | (titr.)[1] | | Reference standard for HPLC |
| 3 | 87.2 | +1.1 | −1.1 | −5.0 | |
| 4 | 82.7 | −0.9 | −2.8 | −6.0 | |
| 5 | 93.7 | −0.5 | ±0.0 | −3.2 | |
| 6 | 83.1 | −4.8 | | | |
| 7 | 90.4 | −3.1 | | | |
| 8 | 85.3 | +1.2 | −6.0 | | |
| 9 | 86.1 | +1.8 | −4.1 | −9.5 | |
| 10 | 78.7 | −3.3 | −8.8 | | |
| 11 | 88.8 | −0.9 | −3.0 | −11.5 | |
| 12 | 75.0 | +0.3 | −5.3 | −5.6 | |
| 13 | 76.4 | +0.9 | −1.6 | −2.8 | |
| 14 | 92.9 | −0.5 | −4.5 | −10.4 | |
| 15 | 90.8 | −2.0 | −2.0 | −9.9 | |
| 16 | 94.6 | +1.4 | +0.1 | ±0.0 | |
| 17 | 90.5 | −0.8 | −5.6 | −12.6 | |
| 18 | 90.9 | +1.5 | +2.1 | −2.6 | |
| 21 | 98.4 | | −0.9 | −1.5** | **8 weeks |
| 25 | 93.2 | | −3.7 | | |
| 26 | 97.7 | +0.2 | −2.7 | −5.1 | |
| 27 | 102.9 | +0.5 | −0.8 | −0.2 | |
| 28 | 95.9 | −0.7 | −1.1 | −4.7 | |
| 29 | 98.7 | +0.9 | +1.3 | +1.0 | |
| 30 | 98.6 | | −0.4 | | |
| Free hyperforin | 91.5 | −17.9 | −24.25 | −28.4 | Comparison |

1 This salt is used as the reference standard. The hyperforin content (in % of the calculated chiometric value) was determined by means of perchloric-acid titration. The values obtained confirm the increased stability and improved storage stability of the hyperforin salts as compared with free hyperforin.

EXAMPLE NO. 33

Activation of Protein Kinase PKCγ by Hyperforin and its Salts.

PKCγ activators are potentially suitable for activating cc-secretase. These activators are found in enzyme tests in which the recombinantly produced PKC-γ is suboptimally active. The test media were:

| | |
|---|---|
| HEPES-NaOH | 50 mM |
| EDTA | 1 mM |
| EGTA | 1.25 mM |
| $MgCl_2$ | 5 mM |
| DTT | 1 mM |
| ATP | 0.1 µM |
| Histon III-S | 100 µg/ml |
| Recombinant PKC-γ | 200–100 ng/well |
| $CaCl_2$ | 1.32 mM |

Table III below presents the activity increases of recombinant PKC-γ due to hyperforin and its salts in various concentrations.

TABLE III

Activation of protein kinase PKC-γ

| | Increase in the activity of PKC-γ [%] at the substance dose: | | |
|---|---|---|---|
| Example No. | 10 µg/ml | 3 µg/ml | 1 µg/ml |
| Hyperforin | 45 | 51 | 6 |
| 1 | 56 | 30 | 9 |
| 5 | 48 | 20 | 3 |
| 21 | 56 | 22 | −9 |
| 24 | 21 | 24 | 7 |
| 25 | 45 | | 12 |
| 26 | 43 | 20 | 10 |
| 27 | 34 | 18 | 6 |
| 31 | 24 | 7 | 5 |
| 1% DMSO | 6 | 5 | 4 |

In the table, the control with 100 nM phorbol-12-myristate-13-acetate (TPA; stimulator of PKC-γ) was set to 100%.

The values determined reveal a distinct increase in the PKC-γ activity when hyperforin or its salts is added to the test medium.

EXAMPLE NO. 34

Activation of α-secretase Due to Hyperforin and its Salts.

In order to be able to demonstrate the α-secretase activity in a cellular test system independently of β- and γ-secretase, an expression plasmid composed of DNA cassettes of APP (Alzheimer Precursor Protein) and APLP-2 (Alzheimer Precursor-like Protein-2) and of the reporter protein Seap (sereted alkaline phosphatase) was designed (see FIG. 1).

As the APP cassette in both constructs begins with amino-acid 7 of the β-amyloid sequence, the recognition sequence for β-secretase in the sec-fusion proteins is absent. Cleavage by γ-secretase has not been described for human APLP-2, with the result that the specificity of the fusion proteins for α-secretase only is achieved by substitution of the transmembrane domain of APLP-2 for APP. The expression plasmid secα1 was stably transfected into human neuronal cells SY5Y. Activation of α-secretase in these secα1-transfected cells is manifested in an increased release of Seap into the cell medium. The quantity of Seap is determined, and serves as a measure of the α-secretase activity.

Test conditions: 80 000 FL-2a cells/well. V=100 μl. Incubation time: 60 min.

Concentration of the substances: 10 μg/ml.

Mean values±s.d. of triplicates.

In Table IV below, the quantities of secreted alkaline phosphatase (Seap) measured in relative light units (RLU) are displayed as a measure of stimulation of the α-secretase activity by hyperforin and its salts.

TABLE IV

Activation of α-secretase

| Example No. | Activity of α-secretase [RLU] | s.d. [RLU] | Comments |
|---|---|---|---|
| Hyperforin | 441 | 55.1 | |
| 21 | 350 | 14.6 | |
| 24 | 445 | 67.1 | |
| 25 | 322 | 128.6 | |
| 26 | 423 | 34.4 | |
| 27 | 453 | 15.1 | |
| 28 | 457 | 42.9 | |
| 29 | 404 | 8.9 | |
| 30 | 419 | 41.9 | |
| 31 | 481 | 42.6 | |
| DMSO | 76 | 8.9 | Solvent control |
| TPA | 386 | 11.4 | Positive control |

The activation of α-secretase by the phorbol ester TPA (100 ng/ml) was measured as the positive control.

The measured values reveal marked activation of α-secretase both when hyperforin and when its salts are added to the test medium.

What is claimed is:

1. Salts of hyperforin and adhyperforin of formula I $$[A^-]_m[B]^{p+} \quad (I)$$

in which
m is a whole number from 1 to 3,

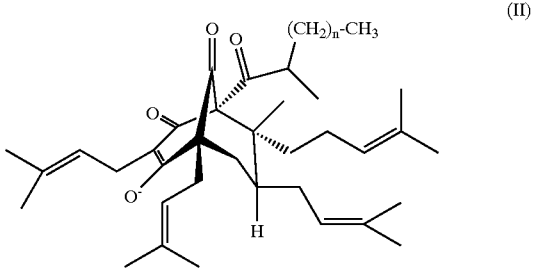

and $[B]^{p+}$ is an ion of an alkali metal or an ammonium ion of a salt-forming nitrogen base of formula III

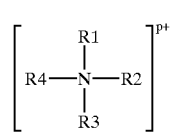

wherein R1, R2 and R3 independently of one another, are a hydrogen atom, a straight-chain or branched alkyl, cycloalkyl, bicycloalkyl, tricycloalkyl, alkenyl, alkynyl, heterocycloalkyl, aryl, heteroaryl, arylalkyl or heteroarylalkyl group, or a derivative of the said groups which include one or more hydroxy, alkoxy, aryloxy, alkanoyl, aroyl, carboxy, alkoxycarbonyl, amino, alkylamino, hydroxylamino, carboxamido having the formula (lower alkyl) —CO—NH—, carbamoyl, ureido, amidino, guanidino, cyano, azido, mercapto, alkylthio, alkylsulphonyl, alkylsulphenyl, aminosulphonyl, fluoro, chloro, bromo, iodo, alkyl or perfluoroalkyl groups, or wherein the residues R1 and R2 together with the N atom are an azetidine, pyrrolidine, pyrroline, piperidine, piperazine, homopiperazine, morpholine, thiomorpholine, pyridine, di- or tetrahydropyridine, pyrimidine, pyrazine, azepine, thiomorpholine, pyridine, di- or tetrahydropyridine, pyrimidine, pyrazine, azepine, dihydroazepine, oxazepine, diazepine, imidazole, pyrazole, oxazole, or thiazole ring, or one of the said rings which exhibits aliphatic, heteroaliphatic, aromatic or heteroaromatic rings condensed on to it and/or is substituted with one or more hydroxy, alkoxy, aryloxy, alkanoyl, aroyl, carboxy, alkoxycarbonyl, amino, alkylamino, hydroxylamino, amido, carbamoyl, ureido, amidino, guanidino, cyano, azido, mercapto, alkylthio, alkylsulphoxy, alkylsuphonyl, alkylsulphenyl, aminosulphonyl, fluoro, chloro, bromo, iodo, alkyl or perfluororoalkyl residue(s), and wherein the residue R4 is a hydrogen atom or a straight-chain or branched alkyl group, in which p=m and give the total number of positive charges of the residue [B].

2. Salts according to claim 1 in which the alkali-metal ion is a lithium, sodium or potassium ion.

3. Salts according to claim 1, in which the salt-forming nitrogen base is selected from the group composed of aliphatic and cycloaliphatic amines, aliphatic and cycloaliphatic amines substituted with one or more hydroxyl groups, polyamines, cyclic and heterocyclic amines, cyclic or heterocyclic amines substituted with one or more lower alkyl or hydroxyl residues, unsubstituted and substituted aromatic, heteroaromatic, arylaliphatic and heteroarylaliphatic amines, and lower alkyl esters, amides or lower alkylamides of natural $\alpha$-, $\beta$-, $\gamma$-, $\delta$-, $\epsilon$-, or $\omega$-amino carboxylic acids.

4. Salts according to claim 3 in which the salt-forming nitrogen base is N,N-dicyclohexylamine.

5. The salts of claim 1 or claim 3 wherein said salt-forming nitrogen base is selected from the group consisting of N,N-dicyclohexylamine, trimethoxybenzylamine, 2-amino-2-methylpropanol, pyrrolidine, N-methyl-D-glucamine, 1-amino-3,5-dimethyladamantane, 4-aminopyridine, L-arginine, L-lysine, Desipramine, and Pindolol.

6. A pharmaceutical preparation for the treatment of Alzheimer's Disease and the symptoms associated with it, comprising a safe and effective amount of at least one salt of any one of claims 1 to 4, together with a pharmaceutically-acceptable carrier.

7. A method of manufacturing the salts of hyperforin and adhyperforin according to one of claims 1 to 4, in which hyperforin and/or adhyperforin are dissolved under inert gas in a solvent or solvent mixture selected from the group composed of $C_5$–$C_8$ alkanes or cycloalkanes, lower chloroalkanes, alcohols, ketones, esters and ethers, and combined in the desired stoichiometric ratio with the solution of an alkali-metal base or a salt-forming nitrogen base in one of the aforementioned solvents or in water, after which the salt formed is allowed to crystallise out and separated or the combined solvents are evaporated and lyophilised after addition of water.

8. A method of enriching or purifying hyperforin and adhyperforin in the form of the salts according to one of claims 1 to 4 from St. John's wort extracts, characterised in that a St. John's wort extract with a total content of hyperforin and adhyperforin of 20–80%, is dissolved in a suitable solvent selected from the group composed of apolar $C_1$–$C_{10}$ alkanes and $C_1$–$C_{10}$ cycloalkanes, and this solution is reacted with an at least equimolar quantity of an alkali-metal base or a salt-forming nitrogen base or a solution of one of these bases in one of the above-mentioned solvents or in a $C_1$–$C_4$ halogenoalkane, ether, tetrahydrofuran or ketone and the salt produced is separated, purified and dried.

9. A method according to claim 8, characterised in that N,N-dicyclohexylamine is used as the base.

10. A method of stabilizing hyperforin, adhyperforin and mixtures thereof comprising obtaining an extract having 20 to 80% hyperforin/adhyperforin dissolved in a suitable solvent, reacting said extract with a nitrogen base to form one or more of the salts as claimed in claim 1, and separating said salts from said reaction mixture.

* * * * *

UNITED STATES PATENT AND TRADEMARK OFFICE
CERTIFICATE OF CORRECTION

PATENT NO.    : 6,444,662 B2
DATED         : September 3, 2002
INVENTOR(S)   : Chatterjee et al.

It is certified that error appears in the above-identified patent and that said Letters Patent is hereby corrected as shown below:

<u>Title page,</u>
Item [73], Assignee, "Willmar Schwabe GmbH & Co." should be
-- Dr. Willmar Schwabe GmbH & Co. --.

<u>Column 24,</u>
Line 3, insert -- [A⁻] is an anion of formula II with n=0 or 1. --
Line 35, after "alkylthio" insert -- alkylsulphoxy --.
Lines 42-44, delete "thiomorpholine, pyridine, di- or tetrahydropyridine, pyrimidine, pyrazine, azepine,"

Signed and Sealed this

Twenty-eighth Day of January, 2003

JAMES E. ROGAN
*Director of the United States Patent and Trademark Office*